United States Patent [19]

Hildenbrand et al.

[11] Patent Number: 4,968,430
[45] Date of Patent: Nov. 6, 1990

[54] COMPOSITE MEMBRANES, PROCESSES FOR THEIR PERPARATION AND THEIR USE

[75] Inventors: Karlheinz Hildenbrand; Rolf Dhein, both of Krefeld; Willi Meister, Dormagen; Dittmar Nerger, Krefeld, all of Fed. Rep. of Germany

[73] Assignee: Bayer Aktiengesellschaft, Leverkusen, Fed. Rep. of Germany

[21] Appl. No.: 327,211

[22] Filed: Mar. 22, 1989

[30] Foreign Application Priority Data

Apr. 7, 1988 [DE] Fed. Rep. of Germany ....... 3811622
Jul. 19, 1988 [DE] Fed. Rep. of Germany ....... 3824359

[51] Int. Cl.$^5$ ............................................. B01D 71/54
[52] U.S. Cl. ................................. 210/640; 210/490; 210/500.27; 210/500.29; 210/500.44
[58] Field of Search ............ 210/640, 500.27, 490, 210/651, 654, 500.41, 500.29; 55/16, 68, 158; 427/245, 246

[56] References Cited

U.S. PATENT DOCUMENTS 4,148,734 4/1979 Hilterhaus et al. ........ 210/500.29 X
4,230,463 10/1980 Henis et al. ................ 210/500.41 X

FOREIGN PATENT DOCUMENTS 0098352 1/1984 European Pat. Off.
2041348 4/1969 France.
2017002 5/1970 France.
2049544 12/1980 United Kingdom.

Primary Examiner—Frank Spear
Attorney, Agent, or Firm—Sprung Horn Kramer & Woods

[57] ABSTRACT

Composite membranes of a macroporous filler-containing membrane of at least two incompatible polymers and a pore-free polyurethane membrane applied there to exhibit an improved action in the removal of benzenes optionally suhstituted by lower alkyl radicals, hydroxyl, chlorine or bromine from their mixtures with aliphatic and/or cycloaliphatic hydrocarbons, alcohols, ethers, ketones and/or carboxylic acid esters or from effluent.

10 Claims, 1 Drawing Sheet

COMPOSITE MEMBRANES, PROCESSES FOR THEIR PREPARATION AND THEIR USE

BACKGROUND OF THE INVENTION

1. Field of the Invention

The invention relates to new composite membranes, processes for their preparation and their use for removing benzenes optionally substituted by lower alkyl radicals, hydroxyl, chlorine or bromine from their mixtures with aliphatic and/or cycloaliphatic hydrocarbons, alcohols, ethers, ketones and/or carboxylic acid esters or from effluent.

Membranes can be used for removal of substance mixtures by permeation. A procedure can be followed here in which, for example, a substance mixture in the liquid phase (feed solution) is brought to one side of the membrane and one substance therefrom, a certain group of substances therefrom or a mixture enriched in the one substance or in he certain group of substances is removed, also in the liquid form, on the one side of the membrane (permeation in the narrower sense). The substance which has passed through the membrane and has been collected again on the other side or the substance mixture described is called the permeate. However, it is also possible to follow the procedure in which, for example, the feed is brought to the one side of the membrane in liquid or gaseous form, preferably in liquid form, and the permeate is removed in the form of a vapour on the other side and is then condensed (pervaporation).

Such permeation processes are useful additions to other processes of substance removal, such as distillation or absorption. Permeation, specifically pervaporation, can be of useful service in particular in the removal of substance mixtures which boil as azeotropes.

2. Description of the State of the Art

There have previously been many attempts to adapt membranes of various polymer materials to individual specific purposes. It is thus known from U.S. Pat. No. 2,953,520 to enrich benzene in the permeate and in this way substantially to separate it off from an azeotropic benzene/methanol mixture with the aid of a non-porous plastic membrane of polyethylene. It is furthermore known from U.S. Pat. No. 3,776,970 to separate the two aromatic compounds styrene and ethylbenzene with the aid of a membrane of certain polyurethane elastomers such that styrene is enriched in the permeate. It is furthermore known from German Patent Specification No. 2,627,629 to remove benzene and alkylbenzenes from aliphatic hydrocarbons, cycloaliphatic hydrocarbons, alcohols, ethers and carboxylic acid esters with the aid of polyurethane membranes.

SUMMARY OF THE INVENTION

It has now been found, surprisingly, that the removal of benzenes optionally substituted by lower alkyl radicals, hydroxyl, chlorine or bromine from their mixtures with aliphatic and/or cycloaliphatic hydrocarbons, alcohols, ethers, ketones and/or carboxylic acid esters or from effluent can be substantially improved using the composite membrane described below in comparison with the polyurethane membranes described in German Patent Specification No. 2,627,629, these improved removal effects becoming particularly clear in the field of mixtures of low aromatic content.

The invention thus relates to composite membranes consisting of
(i) a macroporous filler-containing membrane of at least two incompatible polymers and
(ii) a pore-free polyurethane (PU) membrane applied to (i).

DETAILED DESCRIPTION OF THE INVENTION

The macroporous membrane according to (i) consists of at least two polymers which are incompatible in solution, that is to say, lead to phase separation in a common solution. Further details on incompatible polymer systems which demix are to be found in the monograph by Paul J. Flory, Principles of Polymer Chemistry, Ithaca, N.Y., (1953). By dispersing insoluble fillers into this unstable mixture, this mixture is converted into a stable homogeneous dispersion. This dispersion is then applied to a substrate as a casting solution. The macroporous filler-containing membrane according to (i) is produced from this casting solution by precipitation coagulation, which is also called phase inversion. This technology of phase inversion is known, for example from H. Strathmann, Trennungen von molekularen Mischungen mit Hilfe synthetischer Membranen (Separations of Molecular Mixtures with the aid of synthetic membranes), Steinkopf-Verlag, Darmstadt (1979) and D. R. Lloyds, Materials Science of Synthetic Membranes, ACS Symp. Ser. No. 269, Washington D.C. (1985).

These publications also describe the typical membrane structures obtained during precipitation coagulation. These are always asymmetric membrane structures with a denser polymer skin on the membrane surface and higher porosities inside the membrane. The pore structure can be finger-like or foamlike, depending on the recipe of the casting solution. By forming the denser polymer skin on the membrane surface, the pore diameters of the conventional membranes are limited and as a rule do not exceed values of about 8–10 $\mu$m.

Homogeneous polymer casting solutions are used as the starting substances in the production of precipitation coagulation membranes of the conventional type, since otherwise unstable membranes are obtained. For this reason, typical membrane casting solutions are formed from a polymer and a solvent or solvent mixture (for example polyamide in dimethylacetamide or cellulose acetate in acetone/formamide).

There have already been attempts to produce membranes having increased permeabilities by specific recipes of the polymer casting solutions. Membranes are described in Chem. Pro. Res. Dev. 22 (1983), 320–326 or in DE-OS (German Published Specification) No. 3,149,976 which have been produced using polymer casting solutions containing water-soluble polymers, such as polyvinylpyrrolidone, which are dissolved out during the coagulation in water and in this way lead to enlarged pores. Membranes of polymer mixtures have also been described. However, the recipes of the corresponding casting solutions are built up in such a way that homogeneous polymer solutions are obtained on the basis of the solubility parameters. For example, EP No. 66,408 describes membranes of a mixture of cellulose acetate and polymethyl methacrylate which have increased permeabilities in comparison with the conventional membranes of one polymer. However, polymer combinations with similar solubility parameters and certain very narrow mixing ratios are depended upon here.

It has now been found, surprisingly, that macroporous membranes of polymers which are incompatible and immiscible per se and which can be processed in any desired mixing ratio to give homogeneous casting solutions if certain insoluble fillers are dispersed in them display the abovementioned better removal effects in association with pore-free polyurethane (PU) membranes applied to them.

For example, if a 20% strength by weight solution of polyurethane in dimethylformamide (PU/DMF solution) and a 20% strength by weight solution of polyacrylonitrile in dimethylformamide (PAN/DMF solution) are mixed, while stirring, phase separation occurs after the mixture has stood for a short while. Such mixtures are unstable and are unsuitable as casting solutions for production of membranes. In contrast, if the same polymer/DMF solutions are combined with simultaneous or subsequent dispersing in of fillers, for example talc, homogeneous stable casting solutions which are suitable for membrane production by the precipitation coagulation method are obtained.

In comparison with the known membranes, the membranes produced from such casting solutions have significantly larger pores on the surface and a very much higher overall porosity.

As electron microscopy photographs of the cross-section of these polymer membranes shows, these are structures with a felt-like build-up, whereas the asymmetric structure build-up of the denser polymer skin on the membrane surface is almost completely suppressed. Average pore diameters of up to 30 μm can to be detected on the membrane surface of a membrane of the above recipe.

The polymer casting solutions required for production of such membrane matrices must fulfil the following conditions:

(a) The solutions of the individual polymer components should not be miscible with one another. With miscible systems, analogously to conventional casting solutions, membrane structures of fine porosity and pronounced asymmetric structure are obtained.
(b) The solvents of the individual polymer components must be miscible with one another.
(c) To convert the immiscible polymer components into homogeneous casting solutions, suitable insoluble fillers, for example inorganic fillers, must be dispersed in them.

The nature of the filler can in some cases be important for the stability and homogeneity of the casting solution. Whereas, for example, casting solutions of PU/PAN mixtures containing titanium dioxide (TiO₂ RKB2 ®, Bayer AG) or barium sulphate (Blanc Fixe Mikron ®, Sachtleben) having specific surface areas of about 3 m²/g (particle size about 0.5–1.0 μm) are less favourable in respect of stability and homogeneity, solutions of the same polymer mixture containing talc (Talc AT 1, Norwegian Talc) show a good homogeneity and dispersion stability.

Similarly good results could also be obtained with very fine-grained fillers of high specific surface area, for example with the titanium dioxide Degussa P25 (about 40 m²/g) or the silicon dioxide Aerosil 200 ® Degussa (200 m²/g). Mixtures of talc with barium sulphate or talc with TiO₂ RKB2 ® or titanium dioxide P25 ®, Degussa, with barium sulphate lead to suitable casting solutions. It was also possible to prepare suitable casting solutions by dispersing in microcrystalline cellulose (for example Arbocel B E 600/30 ®, J. Rettenmaier & Söohne). Other suitable fillers are $CaCO_3$, $MgCO_3$, ZnO and iron oxides.

The function and action of the filler is conversion of the unstable inhomogeneous polymer solution into stable and homogeneous casting solutions; the mechanism of this "solubilization" is unknown.

The pore size is controlled via the choice of polymers and the particular quantities. The fillers have only a minor influence, if any, on the pore size. The particle diameters of the fillers are of a much smaller order of size ($\leq 5$ μm) than the pore diameters of the polymer membrane ($\leq 30$ μm). The process of precipitation coagulation in combination with the type of casting solutions described here is responsible for the pore formation of the membranes according to the invention. The range of the average pore size of the macroporous membranes according to the invention is 10 to 30 μm, preferably 15 to 25 μm. Such an average pore size does not exclude the occurrence of pores in a range below (for example from 1 μm) and in a range above (for example up to 50 μm).

The following polymer classes, for example, can be used to produce the macroporous filler-containing membrane according to (i): cellulose esters, polyvinyl esters, polyurethanes, polyacrylic derivatives and acrylic copolymers, polycarbonates and their copolymers, polysulphones, polyamides, polyimides, polyhydantoins, polystyrene and styrene copolymers, poly(-para-dimethyl-phenylene oxide), polyvinylidene fluoride, polyacrylonitrile and ethylene/vinyl acetate copolymers containing at least 50% by weight of vinyl acetate.

Preferably, two or three incompatible polymers from the class of polyurethanes, polyacrylonitrile, polyvinyl acetate, polystyrene, polysulphone, polyvinylidene fluoride, polyamide, polyhydantoin and ethylene/vinyl acetate copolymers containing at least 50% by weight of vinyl acetate are employed. Examples of binary incompatible polymer systems are:

cellulose esters/polyvinyl esters (such as the cellulose acetate Cellidor CP ®/the polyvinyl acetate Mowili ®)
polyurethane/polyacrylic derivatives (such as Desmoderm KBH ®/the polyacrylonitrile Dralon T ® or Desmoderm KBH ®/amino-modified Dralon or Desmoderm KBH ®/anionically modified Dralon U ®, that is to say provided with sulphate groups)
polycarbonate copolymers/polyurethane (such as polyether polycarbonate/Desmoderm KBH ®)
polyvinyl derivatives/polysulphones (such as polyvinylidene fluoride/the polysulphone Udel P 1700 ®)
polyamides or polyimides/polystyrene or styrene copolymers
poly(para-dimethyl-phenylene oxide)/polyvinylidene fluoride and
polyhydantoin/polystyrene.

Other two-component combinations which may be mentioned are: Dralon U ®/Mowilith ® and Cellidor CP ®/Dralon U ®; examples of ternary polymer mixtures are Cellidor CP ®/Dralon U ®/polystyrene, Mowilith R ®/Desmoderm KBH ®/polyvinyl chloride and Desmoderm KBH ®/Mowilith R ®/Dralon T ®, it also being possible for Dralon T ® to be replaced by Dralon A ®.

Preferred binary and ternary polymer systems are: Desmoderm KBH ®/Dralon T ®, Desmoderm KBH ®/Dralon A ®, Desmoderm KBH ®/Mowilith/Dralon T ®, it also being possible for Dralon T ® to be replaced by Dralon A ® or Dralon U ®.

The chemical structures of the polymers preferably employed are described in the appendix to the embodiment examples.

The ratio of the amounts of the polymers, which is required for the pore diameters, in the particular combinations can be determined by appropriate experiments.

If the polymers, of which there are at least two, are mixed in approximately the same amounts, as a rule higher values for the average pore sizes are obtained; if the amounts differ relatively widely, lower values are obtained. The polymer casting solution should contain at least 10% by weight of one polymer based on the total amount of all the polymers.

Dimethylformamide (DMF) is a particularly suitable solvent for the preparation of casting solutions of the preferred polymer combinations. Other suitable solvents are, depending on the polymers used: N-methylpyrrolidone (NMP), dimethyl sulphoxide (DMSO), dimethylacetamide, dioxolane, dioxane, acetone, methyl ethyl ketone or Cellosolve ®.

The amount of solvent is chosen such that a viscosity of the casting solution which reaches the range from 500 to 25,000 mPas is achieved. As a rule, this corresponds to a polymer content of 10 to 40% by weight in the overall casting solution.

In addition to the fillers already mentioned above, there may also be mentioned zeolites and bentonites, and furthermore mixtures of $TiO_2$ with $BaSO_3$ or talc with $BaSO_4$, and furthermore mixtures of $TiO_2$ of large and small specific surface area, such as $TiO_2$ RKB2 ® Bayer/$TiO_2$ P 25 ® Degussa. Preferred fillers are: talc, microcrystalline cellulose, zeolites, bentonites, $BaSO_4$, $TiO_2$ and $SiO_2$.

The overall process for the preparation of content (i) in the composite membranes according to the invention can be described with the aid of a preferred example as follows: The DMF polymer solutions, in each case about 20% strength by weight, of Desmoderm KBH ®, Mowilith ® and Dralon T ® were mixed with the aid of a high-speed stirrer (dissolver) to give a homogeneous polymer casting solution, talc being dispersed in. After degassing in vacuo, this casting solution was applied in a layer thickness of, for example, 150 μm with the aid of a doctor blade to a carrier substrate and was dipped in the coagulation bath, for example pure water. After a residence time of about 2 minutes, the microporous filler-containing membrane formed in this way was removed from the coagulation bath and dried with warm air.

Surfactants, for example dioctyl sodium sulphosuccinate or dodecylbenzenesulphonates, can also be used to prepare the casting solution. Water-soluble polymers, such as cellulose ethers, polyethylene glycols, polyvinyl alcohol or polyvinylpyrrolidone can also be a constituent of the polymer casting solution. Other possible additives are so-called coagulation auxiliaries, such as, for example, cationic polyurethane dispersions (such as Desmoderm Koagulant KPK ®).

The carrier substrates used for application of the casting solution can be one which merely serves for the production of the macroporous filler-containing membrane according to (i) and is therefore peeled off again after the coagulation operation on (i). For this purpose, the carrier substrate must be smooth and is, for example, glass, a polyethylene terephthalate film or a siliconized carrier material. However, if the composite membrane according to the invention of (i) and (ii) is to be provided with a support material for improving the mechanical stability, materials which are permeable to liquid, such as woven polymer fabric or polymer nonwovens, to which the macroporous filler-containing membrane (i) shows good adhesion are used as the carrier substrate. The co-use of such a support material (woven fabric or non-woven) is preferred for the composite membranes according to the invention.

It is furthermore known, for increasing the surface area of membranes, also to use these in the form of tubes, hoses or hollow fibres, as well as in the form of films, production of which has just been described. These tubes, hoses or hollow fibres can be arranged and used in special separation units, which are called modules, in order to achieve maximum membrane surface areas with the minimum possible apparatus volumes. Such tubes, hoses or hollow fibres can be produced, for example, by forcing the filler-containing and in this way stabilized casting solution described above through the outer annular gap of a concentric two-component die, whilst a coagulating agent, such as water, is forced through the central die opening and the casting solution which issues moreover enters a coagulation bath, such as water; coagulation is in this way performed from the inside and from the outside.

After coagulation and drying, a pore-free polyurethane (PU) membrane is applied to the macroporous filler-containing membrane (i) by the casting technique.

The thickness of this pore-free PU membrane is 0.5–500 μm, preferably 5–50 μm.

Polyurethanes for this pore-free PU membrane (ii) and their preparation are known. Polyurethanes are in general prepared by reaction of higher molecular weight di- or polyhydroxy compounds and aliphatic, araliphatic or aromatic di- or polyisocyanates and if appropriate so-called chain-lengthening agents.

Examples which may be mentioned of starting materials containing OH end groups are: polyesters of carbonic acid and aliphatic dicarboxylic acids having 2–10 C atoms, preferably of adipic and sebacic acid, with aliphatic dialcohols having 2–10 C atoms, preferably those having 2 to 6 C atoms, it also being possible for the dialcohols to be used as a mixture in order to lower the melting points of the polyesters; polyesters of low molecular weight aliphatic lactones and ω-hydroxycarboxylic acids, preferably of caprolactone or ω-hydroxycapric acid, the carboxyl groups of which have been reacted with diols; and furthermore polyalkylene etherdiols, specifically polytetramethylene etherdiols, polytrimethylene etherdiols, polypropylene glycol or corresponding copolyethers.

Aromatic diisocyanates, such as toluylene diisocyanate and m-xylylene diisocyanate, araliphatic diisocyanates, such as diphenylmethane 4,4'-diisocyanate, or aliphatic and cycloaliphatic diisocyanates, such as hexamethylene diisocyanate and dicyclohexylmethane 4,4'-diisocyanate, as well as isophorone diisocyanate, are used as the diisocyanates.

If appropriate, these starting materials can also be reacted with dialcohols which are additionally employed, to give so-called prepolymers, and these can then be polymerized again with further di- or polyhydroxy compounds and di- or polyisocyanates and if appropriate further chain-lengthening agents. In addition to the two-dimensionally crosslinked polyurethanes obtainable by using diols and diisocyanates, three-dimensionally crosslinked polyurethanes can also be obtained if trihydroxy compounds and/or polyols and/or tris- and/or polyisocyanates are simultaneously used as starting materials in the polymerization.

Three-dimensional crosslinking can also be achieved, however, if two-dimensionally crosslinked polyurethanes which still contain free hydroxyl and/or isocyanate groups are subsequently further reacted with trifunctional alcohols and/or isocyanates. Such three-dimensionally crosslinked polyurethanes can likewise be obtained by subsequent reaction of two-dimensionally crosslinked polyurethanes containing free isocyanate end groups with small amounts of polymers having end groups containing reactive hydrogen atoms, such as formaldehyde resins or melamine resins. Film-forming elastic polyurethanes are preferably used for the pore-free PU membranes (ii), these being prepared as so-called "one-component PU" with a characteristic number(equivalent)

$$\frac{NCO}{OH} \text{ or } \frac{NCO}{OH + NH_2}$$

of about 1.0, for example in the range from 0.95 to 1.1. Butane-1,4-diol adipic acid polyester, hexamethylene 1,6-glycol adipic acid polyester and hexane-1,6-diol poly-carbonate, in particular, are employed here as diols.

Preferred diisocyanates are isophorone diisocyanate, 4,4'-diisocyanato-diphenylmethane and toluylene diisocyanate. Ethylene glycol, butane-1,4-diol, ethanolamine and diamino-dicyclohexyl-methane are preferably used as chain-lengthening agents.

This group also includes polyurethanes which are prepared from a prepolymer having free hydroxyl groups, a diol and a diisocyanate with a characteristic number $$\frac{NCO}{OH} \text{ of about}$$

Another preferred group of such film-forming polyurethanes are so-called "two-component PUs" of one of the abovementioned polyurethanes, which have been crosslinked by subsequent further polymerization with a polyol, such as trimethylolpropane, and if appropriate a chain-lengthener, such as butylene 1,3-glycol, and a diisocyanate. This group of "two-component PUs" also includes those polyurethanes which have subsequently been further crosslinked with formaldehyde resins or melamine resins.

Other polyurethanes can of course also be used for the production of the pore-free PU membranes (ii) such as are used in the composite membranes according to the invention; only those polyurethanes which dissolve in the aromatic and aliphatic or cycloaliphatic hydrocarbons to be separated are unsuitable.

In addition to the abovementioned casting technique for application of the pore-free PU membrane (ii) onto the microporous filler-containing membrane (i), application by extrusion, calendering or the injection moulding technique is in principle also conceivable. However, application by the casting technique is preferred.

Within the casting technique, a possible embodiment is to add acrylates to the PU casting solution. These added acrylates enable the pore-free PU membrane (ii) to crosslink within the composite membranes according to the invention by UV irradiation or Y radiation or electron beams and in this way to be stabilized mechanically.

Possible acrylates are acrylic acid esters and/or methacrylic acid esters of diols having 4-12 C atoms or of tri- or tetraalcohols, in particular butane-1,4-diol acrylate, butanediol bis-methacrylate, and in particular trimethylolpropane trisacrylate, trimethylolpropane trimethacrylate, pentaerythritol tetraacrylate or pentaerythritol tetramethacrylate, or urethane acrylates (for example reaction products of trimethylolpropane, isophorone diisocyanate and hydroxyethyl acrylate). Their amount is 4-24% by weight, based on the total amount of polyurethane and acrylates. A crosslinkable acrylate/polyurethane blend is thus obtained for (ii). Trimethylolpropane trisacrylate is particularly preferably employed.

If aqueous PU dispersions (Angew. Makromolek. Chemie 98 (1981) 133-165) are used for the production of the pore-free PU membrane (ii), these can be crosslinked with carbodiimides, if appropriate, in order to improve the mechanical strength.

Plasticizers, such as nonylphenol, or fillers, such as finely divided $SiO_2$ (for example silica gel or Aerosil grades from Degussa) and zeolites, can furthermore also be used for production of the PU membrane (ii).

The invention furthermore relates to production of composite membranes of the abovementioned type, which is characterized in that (a) an insoluble filler is dispersed in a solution containing at least two incompatible polymers in amounts which lead to phase separation in the solution, a homogeneous casting solution being formed, (b) this solution is processed to membranes in the form of films, tubes, hoses or hollow fibres and precipitation coagulation is carried out and (c) a pore-free PU membrane is applied to the macroporous filler-containing membrane obtained in this way.

In the production of the membranes in step (b) in the form of films, the solution is applied to a carrier substrate and, after the precipitation coagulation in the manner described above before step (c) is carried out, the coagulate is detached from the carrier substrate.

Preferably, however, this process is modified so that the carrier substrate is a support material of the type mentioned, which remains on the composite membrane. The pore-free PU membrane (ii) is then applied in the casting process in the manner described above.

In the case where the composite membranes according to the invention are produced in the form of tubes, hoses or hollow fibres, after production of the macroporous filler-containing membrane (i), for example by extrusion and coagulation in the manner described above, a PU casting solution is applied to the inside of such tubes, hoses or hollow fibres by casting in order to produce the pore-free PU membrane (ii), the system being subsequently flushed with an inert gas, if appropriate, for example in order to avoid sticking of the inside in the case of hollow fibres. This inert gas can at the same time be prewarmed in order to effect evaporation of the solvent from the casting solution. Such a method of application of (ii) is suitable for bringing the mixture to be separated, of benzenes optionally substituted by lower alkyl radicals, hydroxyl, chlorine or bromine and aliphatic and/or cycloaliphatic hydrocarbons, alcohols, ethers, ketones and/or carboxylic acid esters, or the effluent containing such benzenes, inside these tubes, hoses or hollow fibres and for removing the permeate enriched in optionally substituted benzene from the outer surface of the tubes, hoses or hollow fibres. This type of build-up of the composite membranes according to the invention is particularly favourable if a pressure gradient from a higher to a lower pressure is to be applied from the mixture side to the permeate side.

In addition, the reverse use is in principle also possible, that is to say bringing of the starting mixture onto the outer surface of the tubes, hoses or hollow fibres and removal of the permeate from the inside surface. For this embodiment, the PU casting solution for the production of (ii) must be brought onto the outer surface of tubes, hoses or hollow fibres of the macroporous filler-containing membrane (i).

The invention furthermore relates to the use of the composite membranes described above for removing benzene, which can be mono-, di- or trisubstituted by chlorine, bromine, $C_1$-$C_4$-alkyl or hydroxyl from aliphatic and/or cycloaliphatic hydrocarbons, alcohols, ethers, ketones and/or carboxylic acid esters or from effluent.

Optionally substituted benzenes are: benzene, toluene, xylene, ethylbenzene, propylbenzene, chlorobenzene, dichlorobenzene, bromobenzene, phenol or cresol.

Examples of aliphatic or cycloaliphatic hydrocarbons from which the optionally substituted benzene is to be removed are, for example, straight-chain or branched hydrocarbons having 5-14 C atoms, such as pentane, hexane, heptane, 2-methyl- and 5-methylhexane, 2,2-dimethylpentane, 2,4-dimethylpentane, 2,2,3-trimethylbutane, straight-chain or branched tetradecane, i-octane or cycloaliphatic hydrocarbons, in particular having 5 and 6 ring C atoms, which can also be substituted by $C_1$-$C_8$-alkyl, preferably $C_1$-$C_4$-alkyl and particularly preferably by methyl and ethyl. These aliphatic or cycloaliphatic hydrocarbons can be present individually or as a mixture; mixtures of petrochemical origin, for example for fuels, are preferably suitable. Preferred cycloaliphatic hydrocarbons in these are methylcyclopentane, cyclohexane and methylcyclohexane. It is also possible for more than one optionally substituted benzene for removal to be present in the mixture.

Possible further organic solvents from which optionally substituted benzenes can be removed with the aid of the membrane according to the invention are alcohols, such as ethanol; ethers, such as dioxane; ketones, such as cyclohexanone, and carboxylic acid esters, such as ethyl acetate.

The removal is by liquid/liquid permeation, gaseous/gaseous permeation or liquid/gaseous pervaporation, preferably by liquid/gaseous pervaporation. The techniques needed for this are known to the expert. Preferably, a pressure gradient in the direction of the permeate is used, for which a reduced pressure (for example 1-500 mbar) is applied to the permeate side.

It is surprising that the composite membranes according to the invention have a significantly improved separation factor for optionally substituted benzenes.

The separation factor $\alpha$, which represents a measure of the selective permeability of the membrane, is generally stated as a measure of the removal effect; it is defined by the following equation:

$$\alpha = \frac{C_{Ap}}{C_{Bp}} \times \frac{C_{Bg}}{C_{Ag}}$$

in which
$C_{Ap}$ and $C_{Bp}$ denote the concentrations of substances A and B in the permeate (p) and
$C_{Ag}$ and $C_{Bg}$ denote the corresponding concentrations in the mixture (g) to be separated,
and wherein
A in each case denotes the component to be removed, in the present case the optionally substituted benzene (or several benzenes) and
B denotes the other or remaining components of the mixture.

A very surprising effect of the composite membranes according to the invention is their successful use for removal of optionally substituted benzene from effluent.

EXAMPLE 1

(a) Production of the macroporous filler-containing polymer blend membrane 21.6 g of a 17% strength Dralon T ®/DMF solution, 65.2 g of a 20% strength KBH ® polyurethane/DMF solution, 86.6 g of a 25% strength Mowilith 50 ®/solution, 22.5 g of sodium dioctyl sulphosuccinate, 14.8 g of talc AT 1, 59.4 g of barium sulphate (Blanc Fixe Mikron), 17.3 g of KPK ® (Bayer AG, cationic polyurethane dispersion) and 140.0 g of DMF were processed to a homogeneous dispersion with the aid of a high-speed stirrer (dissolver). After degassing in vacuo, this casting solution was coated in a layer thickness of 150 µm with the aid of a doctor blade onto a polypropylene non-woven 200 µm thick (type FO 2430 from Freudenberg) and coagulated in water at 45° for 3 minutes. The polymer matrix formed in this way and resting on the carrier film was dried by means of warm air.

(b) Application of the pore-free PU membrane: (production of the composite membrane according to the invention)

The porous membrane matrix obtained according to (a) was coated with the following polyurethane: 100.0 g of poly-hexanediol adipate (average molecular weight about 850), 57.5 g of isophorone diisocyanate and 23.7 g of isophoronediamine were reacted with one another in a known manner. A 30% strength solution (weight/volume) of this polyurethane in a mixture of toluene and isopropanol (1:1) was filtered through a pressure filter and the filtrate was left to stand until it was free from bubbles. This polyurethane casting solution was applied with a wet application of 100 µm onto the macroporous carrier membrane described in (a). The solvent was removed with the aid of warm air; the composite membrane No. 2 characterized in FIGS. 1 and 2 was in this way obtained.

Figure 1:
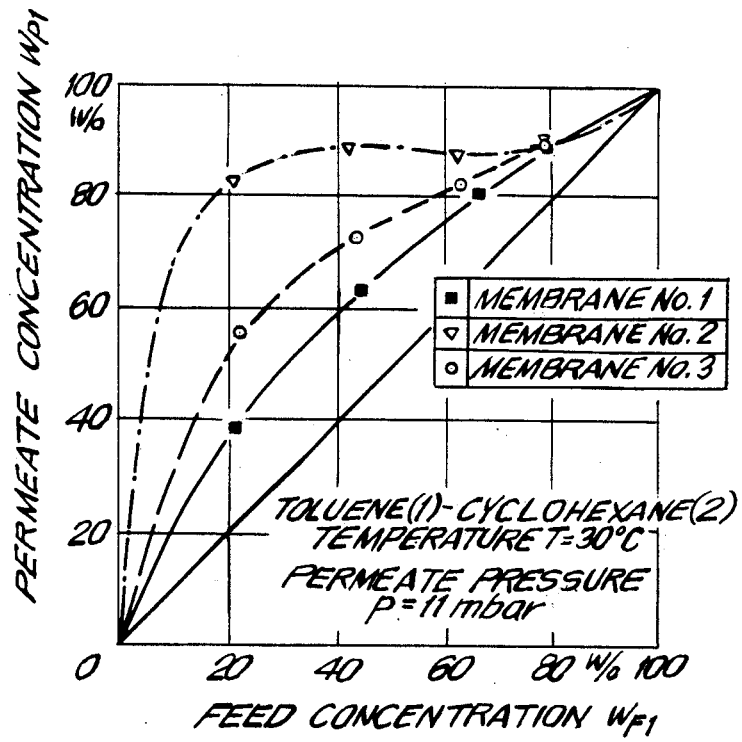
FIGS. 1 and 2 are graphs depicting the separation effect and flow characteristics of the membranes according to Examples 1 to 3 (membrane No. 1: pore-free (PU) membrane; membrane No. 2: composite membrane according to the invention; membrane No. 3: pore-free PU membrane combined with a polyamide membrane).
Figure 2:
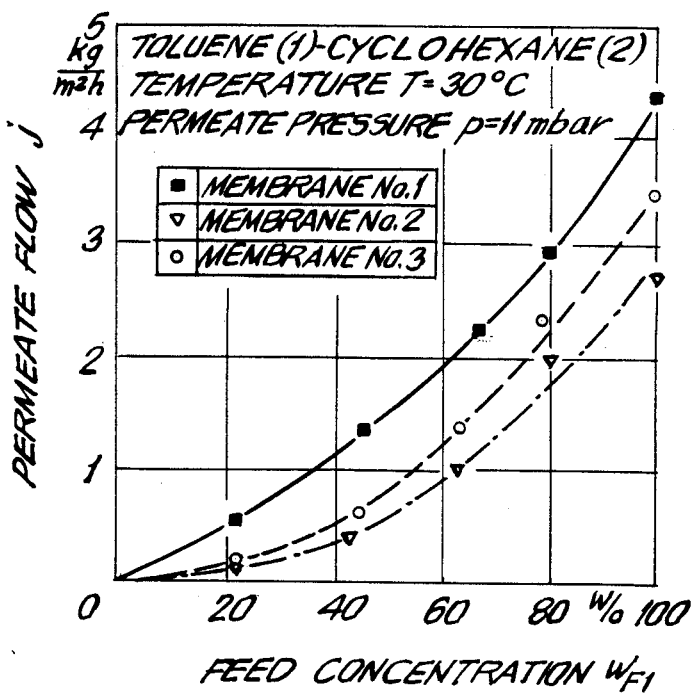

The membrane characterized in FIGS. 1 and 2 (for comparison) was obtained by coating a polyamide microfiltration (MF) membrane (Pall, 0.2 μm) with the same polymer casting solution according to (b) under the same production parameters.

EXAMPLE 2

(for comparison)

Production of the carrier-tree polyurethane pervaporation membrane

The polymer solution described in Example 1(b) was coated in a layer thickness of 100 μm onto a transparent polyethylene terephthalate film (PET film). The solvent was removed by evaporation with warm air; the membrane film adhering to the PET film was in this way obtained. Membrane No. 1 characterized in FIGS. 1 and 2 was obtained by careful peeling off from the PET film.

EXAMPLE 3

Production of a composite membrane with a pore-free acrylate/polyurethane blend separating layer 3.75 g of trimethylolpropane triacrylate (commercial product from Rohm) and 0.18 g of 1-hydroxycyclohexylphenyl ketone (Irgacure 184 ®, commercial product from Ciba-Geigy), as a photoinitiator, were added to a polyurethane casting solution of 25.0 g of polyurethane (chemical structure as in Example 1(b), 37.5 g of toluene and 37.5 g of isopropanol.

The mixture was homogenized by stirring and left to stand for degassing. This casting solution was then applied in a layer thickness of 150 μm to the polymer blend membrane described in Example 1(a) and the solvent was subsequently evaporated off. The pore-free acrylate/polyurethane blend layer formed in this way was crosslinked with the aid of UV light.

| Exposure conditions | |
|---|---|
| Exposure apparatus | Hanovia |
| Radiation source | medium-pressure mercury vapour lamp |
| Lamp output | 80 W/cm |
| Distance between sample and lamp | 11 cm |
| Belt speed | 10 m/minute |

The separation effect and flow characteristics of this membrane during toluene/cyclohexane separation corresponded to those of the membrane described in Example 1 (FIG. 1). However, improved membrane stabilities could be observed at high temperatures.

EXAMPLE 4

Toluene/cyclohexane separation

The membranes described in Examples 1 and 2 were tested with the aid of a pervaporator module, such as is described, for example, in DE-OS (German Published Specification) No. 3,441,190, under the same conditions by allowing feed solutions of various compositions to flow over. The experimental conditions and the experimental results are shown in FIGS. 1 and 2.

The increase in selectivity when the macroporous polymer blend membrane is used according to the invention as a composite component is striking. Whereas the composite membrane according to the invention remained fully functional for several days at 50° C., polyurethane membrane No. 1 dissolved after a few hours under these conditions.

Explanatory note on FIGS. 1 and 2:

The composition of the substance mixture to be separated (feed) as a function increasing toluene content is in each case shown on the abscissa. The permeate concentration with increasing toluene content is shown on the ordinate in FIG. 1 and the corresponding permeate flow is shown on the ordinate in FIG. 2. Composite membrane No. 2 according to the invention shows an unexpected increase in selectivity (increase in the separation factor α), especially in the regin of low toluene concentrations. The macroporous filler-containing membrane (i) of at least two incompatible polymers thus contributes towards the selecting effect, although it places no resistance against the feed because of the macroporous structure and thus displays no corresponding separation action in accordance with the concept of the solubility/diffusion model. The composite membrane according to the invention is additionally overall more mechanically and chemically stable, even at higher temperatures.

EXAMPLE 5

Removal of chlorobenzene from an effluent

The feed solution to be purified was an effluent which contained 10% of ethanol and 150 ppm of chlorobenzene. Composite membrane No. 2 from Example 1 was used. The feed solution was kept static (without flowing over) on the membrane (temperature=30° C.; permeate pressure p=11 mbar).

After 4 hours of testing, the content of chlorobenzene in the feed solution had been reduced to 0.02 ppm.

EXAMPLE 6

Separation of benzene/cyclohexane

Composite membrane No. 2 from Example 1 was used. Composition of the feed solution: 55% of benzene, 45% of cyclohexane.

The experiment was carried out as in Example 3. A flow of 0.6 L/m$^2$×hour was determined. Only traces (<0.5% of cyclohexane) could be found in the permeate.

APPENDIX

Chemical structures of the polymers preferably used

Polyurethane (KBH ®, Bayer AG)

Thermoplastic polyadduct which was obtained by reaction of 75 parts of a polyester of adipic acid, ethylene glycol and 1,4-butanediol (molecular weight=2,000), 25 parts of a polyester of adipic acid and 1,4-butanediol (molecular weight=2,250), 25 parts of 1,4-butanediol and 85 parts of diphenylmethane 4,4'-diisocyanate.

Dralon T ® (Bayer AG)

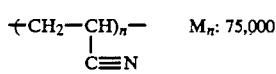

$M_n$: 75,000

Dralon U ® (Bayer AG)

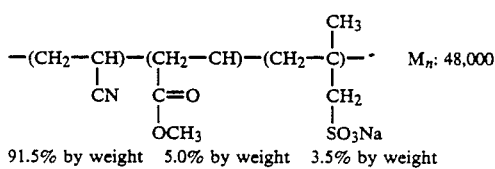

$M_n$: 48,000

91.5% by weight   5.0% by weight   3.5% by weight

Dralon A ® (Bayer AG)

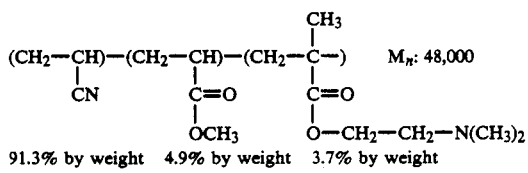

91.3% by weight    4.9% by weight    3.7% by weight

Mowilith 50 ® (Polyvinyl acetate, Hoechst AG)

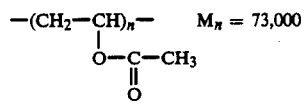

Cationic polyurethane dispersion (KBK ®, Bayer AG)

The polyurethane dispersion serves as a coagulation auxiliary and is a cationic emulsifier-free dispersion of a reaction product of 200 parts of a polyester of adipic acid, phthalic acid and ethylene glycol (molecular weight=1,700), 50 parts of toluylene diisocyanate, 20 parts of N-methyldiethanolamine and 6 parts of p-xylylene dichloride.

What is claimed is:

1. Composite membranes, comprising (i) a macroporous filler-containing membrane of at least two incompatible polymers and (ii) a pore-free polyurethane (PU) membrane applied to (i) said composite membranes, being prepared by (a) dispersing an insoluble filler in a solution containing said at least two incompatible polymers, the amounts of said polymers being such as which would normally lead to phase separation in the solution to form a homogeneous casting solution, (b) processing said solution into membranes and carrying out precipitation coagulation thereof and (c) applying a pore-free PU membrane to the macroporous filler-containing membrane so obtained.

2. Composite membranes according to claim 1, wherein two or three incompatible polymers selected from the group consisting of polyurethanes, polyacrylonitrile, polyvinyl acetate, polystyrene polysulphone, polyvinylidene fluoride, polyamide, polyhydantoin and ethylene/vinyl acetate copolymers containing at least 50% by weight of vinyl acetate are used for (i).

3. Composite membranes according to claim 1, wherein one ore more fillers selected from the group consisting of talc, microcrystalline cellulose, zeolites, bentonites, $SiO_2$, $TiO_2$ and $BaSO_4$ are used.

4. Composite membranes according to claim 1, additionally containing a support material onto which (i) and then (ii) are applied.

5. Composite membrane according to claim 1, wherein the pore-free membrane (ii) is a crosslinked acrylate/polyurethane blend.

6. Composite membranes according to claim 5, wherein the acrylates are one or more esters of acrylic acid or methacrylic acid with aliphatic, cycloaliphatic or aralphatic diols and/or polyols having three of more OH groups, the diols having 4–12 C atoms.

7. Composite membranes according to claim 6, wherein the acrylates are butane-1,4-diol acrylate, butanediol bis-methacrylate, trimethylolpropane trisacrylate, trimethylolpropane trimethylacrylate, pentaerythritol tetraacrylate of pentaerythritol tetramethacrylate, or urethane acrylates.

8. Composite membranes according to claim 7, wherein the acrylate is trimethylolpropane trisacrylate.

9. Composite membrane according to claim 1, wherein a support material which remains on the composite membrane is used as the carrier substrate for casting the solution containing the incompatible polymers and fillers during production of the composite membranes in the form of films.

10. A process for removing benzene, said benzene being optionally mono-, di- or trisubstituted by chlorine, bromine, hydroxyl or $C_1$–$C_4$-alkyl, from aliphatic and/or cycloaliphatic hydrocarbons, alcohols, ethers, ketones and/or carboxylic acid esters or from effluent by permeation through a composite membrane the improvement wherein said removal is carried out using the composite membrane according to claim 1.

* * * * *